United States Patent [19]

Gompf et al.

[11] 4,283,472

[45] Aug. 11, 1981

[54] SILVER HALIDE ELEMENTS CONTAINING BLOCKED PYRAZOLONE MAGENTA DYE-FORMING COUPLERS

[75] Inventors: Thomas E. Gompf; Howell A. Hammond; Jared B. Mooberry, all of Rochester, N.Y.

[73] Assignee: Eastman Kodak Company, Rochester, N.Y.

[21] Appl. No.: 124,872

[22] Filed: Feb. 26, 1980

[51] Int. Cl.³ .............................................. G03C 7/00
[52] U.S. Cl. ..................................... 430/17; 430/381; 430/386; 430/387; 430/548; 430/554; 430/555; 430/558
[58] Field of Search .............. 430/548, 554, 558, 381, 430/386, 387, 555, 17

[56] References Cited

U.S. PATENT DOCUMENTS

| T887,007 | 6/1971 | Dallon et al. | 430/558 |
|---|---|---|---|
| 2,436,130 | 2/1948 | Weissberger et al. | 430/558 |
| 2,575,182 | 11/1951 | Martin | 430/558 |
| 2,706,685 | 4/1955 | Salminen | 430/554 |
| 2,865,748 | 12/1958 | Feniak et al. | 430/554 |
| 3,888,680 | 6/1975 | Fujiwhara et al. | 430/558 |
| 4,123,281 | 10/1978 | Monbaliu et al. | 430/554 |
| 4,130,427 | 12/1978 | Monbaliu et al. | 430/558 |

FOREIGN PATENT DOCUMENTS 2331066 6/1977 France .
1335730 10/1973 United Kingdom .
1546837 5/1979 United Kingdom .

*Primary Examiner*—J. Travis Brown
*Attorney, Agent, or Firm*—Joshua G. Levitt

[57] ABSTRACT

Novel 5-pyrazolone magenta dye-forming couplers are blocked with a coupler moiety which yields an alkali-soluble or colorless reaction product. The coupler moiety is joined via its coupling position to the enol oxygen of the 5-pyrazolone and is displaced therefrom during processing as a result of reaction by means of oxidized color developing agent to thereby activate the 5-pyrazolone coupler. These couplers have good reactivity and good resistance to aerial contaminants, such a formaldehyde, and can be incorporated in photographic emulsions and elements.

18 Claims, No Drawings

SILVER HALIDE ELEMENTS CONTAINING BLOCKED PYRAZOLONE MAGENTA DYE-FORMING COUPLERS

This invention relates to novel pyrazolone magenta dye-forming couplers, to photographic silver halide emulsions and elements containing these couplers, to processes of forming magenta dye images with elements containing these couplers and to processed elements containing magenta dyes derived from these couplers.

Color images are customarily obtained in the photographic art by reaction between the oxidation product of a silver halide color developing agent (i.e., oxidized aromatic primary amino developing agent) and a dye forming compound known as a coupler. The reaction between coupler and oxidized color developing agent results in coupling of the oxidized color developing agent at a reactive site in the coupler, known as the coupling position, and yields a dye. The dyes produced by coupling are indoaniline, azomethine, indamine, or indophenol dyes, depending upon the chemical composition of the coupler and the developing agent. The subtractive process of color formation is ordinarily employed in multicolored photographic elements and the dyes produced by coupling are usually cyan, magenta and yellow dyes which are formed in or adjacent silver halide emulsion layers sensitive to radiation absorbed by the image dye, i.e., silver halide emulsion layers sensitive to the red-, green- or blue regions of the spectrum.

The couplers typically employed to produce magenta dyes are 5-pyrazolones. They yield azomethine dyes upon coupling with oxidized aromatic primary amino developing agents. In such couplers, the coupling position, i.e., the site at which oxidized color developing agent reacts, is the active methylene group in the 4-position of the coupler. This active methylene group can be substituted or unsubstituted.

Many of the color forming couplers employed in photographic materials are 4-equivalent couplers. In other words, they require development of four molecules of silver halide in order to ultimately produce one molecule of dye. Also known are 2-equivalent, 6-equivalent and 8-equivalent couplers which require development of two, six or eight molecules of silver halide, respectively, to produce one molecule of dye.

5-Pyrazolone couplers in which the enol oxygen is blocked with an acyl group are described in U.S. Pat. Nos. 2,575,182, 2,706,685 and 4,123,281 and in U.S. Defensive Publication T887007. These patents and the publication indicate that blocking the enol oxygen with an acyl group reduces or eliminates problems associated with the reactivity of 5-pyrazolones such as self-condensation of the pyrazolone to yield colored products, susceptibility to oxidation, reactivity with hardeners and the like. These patents also indicate that to activate the methylene group in the four position of the pyrazolone, and thus render the compound capable of coupling to yield a dye, the acyl group should be eliminated and that this can be accomplished by pretreatment with an alkaline solution or by alkaline hydrolysis during color development. With couplers blocked in this way, it is necessary to choose between good reactivity and good storage stability in selecting a blocking group. For the coupler to have good reactivity, the blocking group must be rapidly removable from the coupler during processing. For the coupler to have good storage stability, the blocking group must be resistant to removal during storage. Acyl blocking groups removable by alkaline hydrolysis do not satisfy both criteria. If the group is rapidly removable during processing, it is susceptible to removal during storage; if the group is resistant to removal during storage, it is removed slowly during processing. Further, with couplers blocked in this way the acyl group is uniformly removed during processing. Thus, coupler in the exposed and processed element which has not reacted with oxidized color developing agent to form a dye is susceptible to self-condensation and reaction with aerial contaminants, leading to stain formation in background areas.

We have found novel 5-pyrazolone magenta dye-forming couplers which have both good reactivity and good storage stability and are resistant to aerial contaminants, especially aerial formaldehyde. The couplers of our invention are 5-pyrazolone magenta dye-forming couplers blocked with a coupler moiety which yields an alkali soluble or colorless reaction product joined via its coupling position to the enol oxygen of the 5-pyrazolone.

With couplers of this invention the 5-pyrazolone magenta dye-forming coupler is unblocked and becomes an active coupler only after the blocking coupler is displaced from the enol oxygen by reaction between the blocking coupler and oxidized color developing agent. This leads to several beneficial results. It permits a blocking group to be selected which will give good storage stability yet which can be rapidly removed by a coupling reaction thus giving good reactivity. It reduces the possiblity of background stain, since in areas where oxidized color developing agent has not been generated during processing the coupler remains blocked. It increases the equivalency of the coupler, since the blocking coupler does not contribute to image dye density, and thereby permits improvements in the granularity of the dye image.

In one embodiment, this invention relates to nondiffusible magenta dye-forming couplers having the structure:

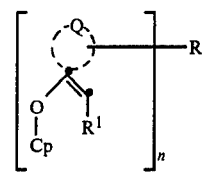

wherein:

Q represents the atoms to complete a 5-pyrazolone magenta dye-forming coupler moiety;

n is 1 or 2;

R is a ballast group when n is 1 or a divalent organic group when n is 2;

$R^1$ is hydrogen or a coupling-off group; and

Cp is a coupler moiety which upon reaction by means of oxidized color developing agent yields a colorless or alkali soluble reaction product and is attached at its coupling position to the enol oxygen of the pyrazolone coupler moiety.

In another embodiment, this invention relates to photographic silver halide emulsions and elements containing magenta dye-forming couplers of this invention.

In yet another embodiment, this invention relates to processes of forming magenta dye images in a photographic element by developing the element in the presence of a magenta dye-forming coupler of this invention.

In still another embodiment, this invention relates to processed photographic elements containing a magenta dye obtained by coupling of oxidized silver halide color developing agent and a coupler of this invention.

In the above structural formula I the 5-pyrazolone coupler moiety completed by Q can be any of the 5-pyrazolone couplers known in the art. A wide variety of such couplers are known and are described in such representative patents as U.S. Pat. Nos. 2,343,703, 2,369,489, 2,600,788, 2,908,573, 3,062,653, 3,152,896 and 3,519,429, and in "Farbkuppler—Eine Literatureubersicht" published in Agfa Mitteilungen, Band II, pp. 126-156 (1961). Typically such couplers are substituted in the one and three positions with alkyl of 1 to 8 carbon atoms, aryl of 6 to 10 carbon atoms, and/or ballasting groups. Preferably, the one position substituent is an aryl group, e.g. phenyl, halophenyl, alkylphenyl, alkoxyphenyl, aryloxyphenyl and the like; and the three position substituent is a ballast group.

When n is 1, R is a ballast group, i.e., an organic radical of such size and configuration as to confer on the coupler molecule sufficient bulk to render the coupler substantially nondiffusible from the layer in which it is coated in a photographic element. Typical ballast groups contain a total of 8 to 40 carbon atoms and include alkyl, aryl, amino and amido groups which can contain such substituents as alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido and sulfamoyl.

When n is 2, two magenta dye-forming coupler moieties are linked together through a divalent organic substituent on the coupler moiety. Such couplers have been referred to in the art as tandem couplers or bis couplers. The divalent organic group through which the coupler moieties are linked can be any of the substituents typically contained in pyrazolone couplers, such as alkylene, arylene and ballast groups. Since joining two coupler moieties in this way increases the bulk and nondiffusibility of the coupler the ballast group can be reduced in size or eliminated. However, it can be retained to confer additional nondiffusibility, and/or as the linkage between the two coupler moieties.

The coupling-off group represented by $R^1$ can be any of the coupling-off groups known in the art. Such groups can alter the equivalency of the coupler, can modify the reactivity of the coupler, or can advantageously affect the layer in which the coupler is coated or other layers in the element by performing, after release from the coupler, such functions as development inhibition, bleach inhibition, bleach acceleration, color correction and the like. Representative coupling-off groups include halogen, alkoxy, aryloxy, heterocyclyloxy, sulfonyloxy, acyloxy, acyl, heterocyclyl, thiocyano, alkylthio, arylthio, heteroylthio, sulfonamido, phosphonyloxy and arylazo. Preferred coupling-off groups are halogen, alkoxy, aryloxy, alkylthio and arylthio.

The coupling-off group represented by $R^1$ can be an additional coupler molecule joined to the coupling position via a linking group attached to the coupling position of the additional coupler molecule. The additional coupler molecule can be the same as the coupler molecule to which it is joined or can be different therefrom.

The linking group can be any group which as a result of a coupling reaction will be cleaved from each of the coupling positions. Representative linking groups include methylene, oxyphenyleneoxy, oxyphenylene-carbonyl-phenyleneoxy and oxyphenylenesulfonyl-phenyleneoxy.

Cp can be any coupler moiety which upon reaction with oxidized color developing agent ultimately yields (1) a reaction product which is soluble in alkaline processing solution so that during processing it is free to diffuse from the element, or (2) a colorless reaction product, so that it does not contribute to final image density. Typical coupling moieties which yield alkali soluble reaction products are yellow and cyan dye-forming couplers which contain acid and/or ester groups to thereby confer alkali solubility upon the reaction product. Examples of coupling moieties which yield colorless reaction products are described in such patents as U.K. Pat. No. 861,138, U.S. Pat. Nos. 3,632,345, 3,928,041, 3,958,993 and 3,961,959 which relates to carbonyl containing compounds that form colorless products on reaction with oxidized color developing agent.

Couplers of this invention in which Cp is an alkali soluble yellow dye-forming coupling moiety are preferred.

Particularly preferred magenta dye-forming couplers of this invention have the structure:

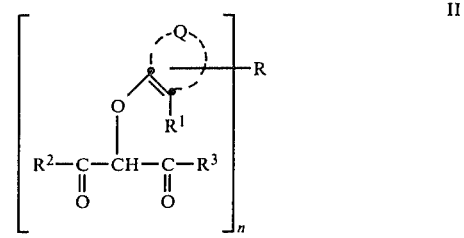

II wherein:

Q represents the atoms to complete a 5-pyrazolone magenta dye-forming coupler moiety;

n is 1 or 2;

R is a ballast group when n is 1 or a divalent organic group when n is 2;

$R^1$ is hydrogen or a coupling-off group and $R^2$ and $R^3$ represent the atoms to complete an alkali soluble yellow dye-forming coupler moiety.

Representative $R^2$ groups are alkyl, e.g. t-butyl, and aryl, e.g. phenyl and alkoxyphenyl. Representative $R^3$ groups are phenylamino groups containing acid or ester solubilizing groups, e.g. carboxy and sulfo groups.

Especially preferred magenta dye-forming couplers of this invention have the structure:

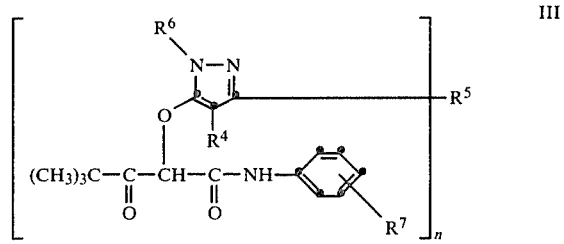

III wherein:

n is 1 or 2;

R⁴ is hydrogen or a coupling-off group;
R⁵ is a monovalent or divalent amino or amido ballast group or an alkylene or arylene group;
R⁶ is aryl; and
R⁷ is one or more acid or ester solubilizing groups.

Especially preferred are compounds of Formula III wherein:

n is 1;
R⁴ is hydrogen, aryloxy or arylthio;
R⁵ is a monovalent amino or amido ballast group; and
R⁶ is phenyl, alkoxyphenyl or halophenyl.

Examples of specific couplers of this invention are shown below.

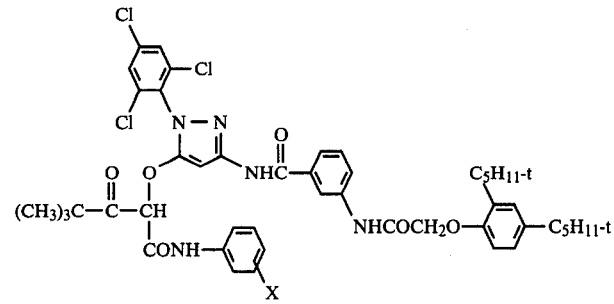

| Coupler No. | X |
|---|---|
| 1 | 3,5-di-COOH |
| 2 | 4-COOH |

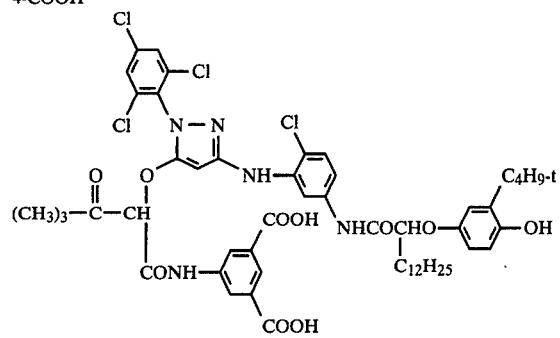

3

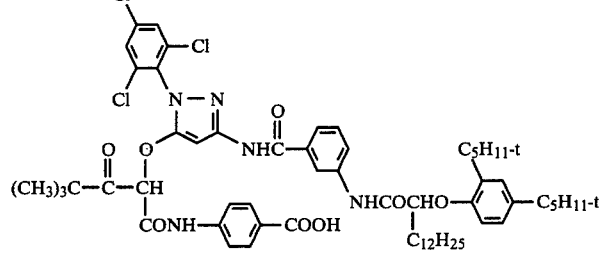

4

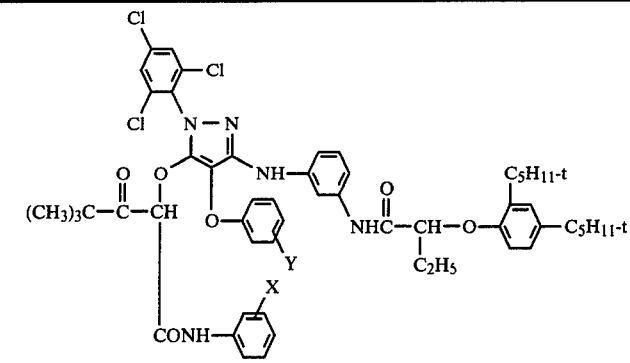

| Coupler No. | X | Y |
|---|---|---|
| 5 | 4-COOH | 4-CH₃ |
| 6 | 4-COOH | H |
| 7 | 4-COOH | 4-OCH₃ |
| 8 | 4-COOH | 4-Cl |
| 9 | 4-COOH | 4-NHCOCH₃ |
| 10 | 4-COOH | 4-CN |
| 11 | 3,5-di-COOH | 4-COOH |
| 12 | 3,5-di-COOH | 4-CN |

-continued
| 13 |
|---|
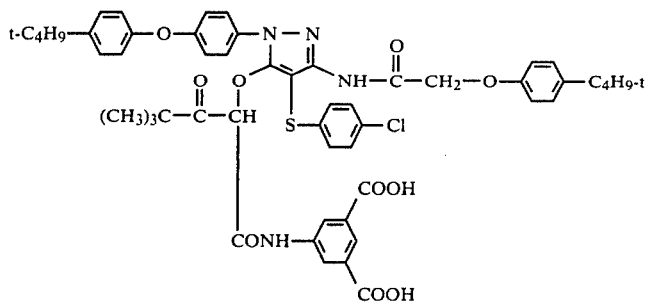
Coupler No.
14
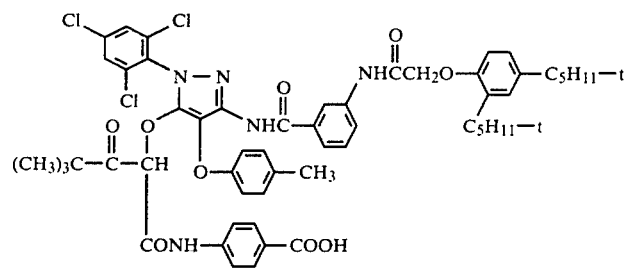
15
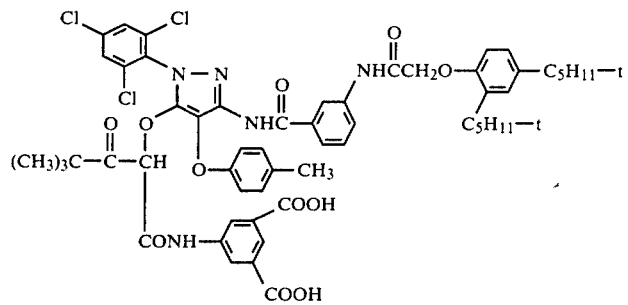
16
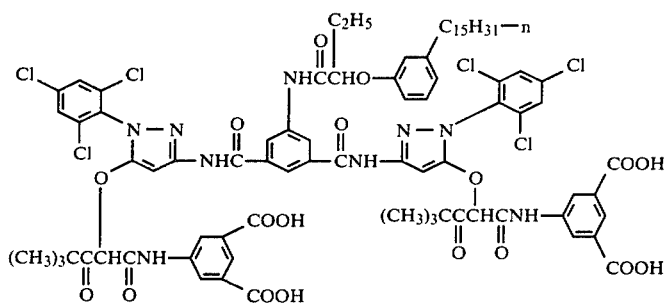
17
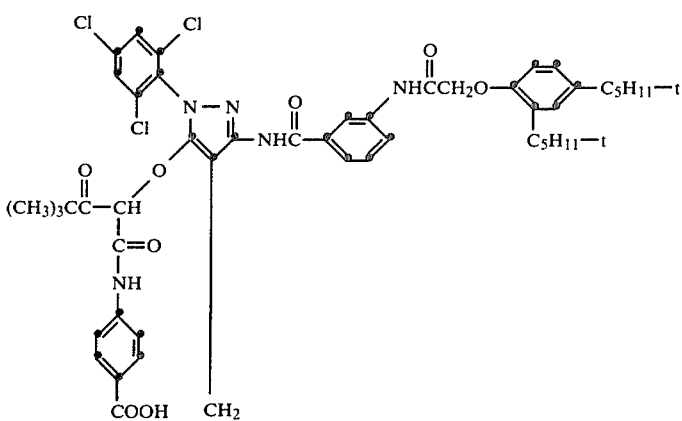

-continued

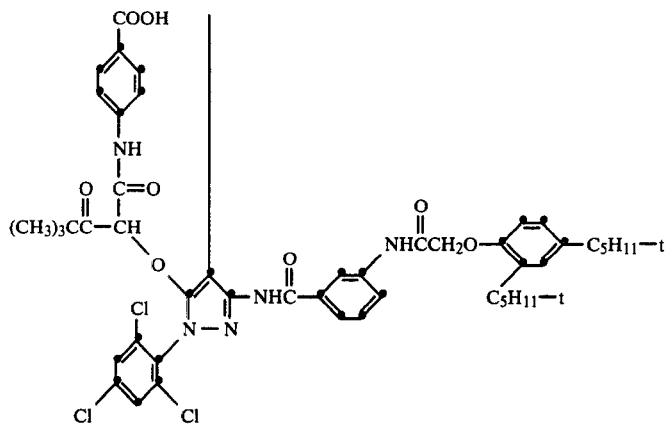

Couplers of this invention can be prepared by condensing 5-pyrazolone magenta dye-forming couplers with an appropriate derivative of the blocking coupler moiety, such as a halo derivative. Ballast groups, and other substituents, can be added either before condensation or subsequent thereto. A representative preparation of a coupler of this invention, including preparation of intermediates, is shown in Example 1.

The magenta dye-forming couplers of this invention can be used in the ways and for the purposes that magenta dye-forming couplers have been previously used in the photographic art. The unique and advantageous properties of these couplers enhance their utility in photographic materials and processes.

Typically, the couplers are incorporated in silver halide emulsions and the emulsions coated on a support to form a photographic element. Alternatively, the couplers can be incorporated in photographic elements adjacent the silver halide emulsion where, during development, the coupler will be in reactive association with development products such as oxidized color developing agent. Thus, as used herein, the term "associated therewith" signifies that the coupler is in the silver halide emulsion layer or in an adjacent location where, during processing, it will come into reactive association with silver halide development products.

The photographic elements can be single color elements or multicolor elements. In a multicolor element, the magenta dye-forming couplers of this invention would usually be associated with a green-sensitive emulsion, although they could be associated with an emulsion sensitized to a different region of the spectrum, or with a panchromatically sensitized, orthochromatically sensitized or unsensitized emulsion. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer, e.g., as by the use of microvessels or cells as described in Whitmore U.S. Patent Application Ser. No. 8,819 filed Feb. 2, 1979.

A typical multicolor photographic element would comprise a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, at least one of the magenta dye-forming couplers being a coupler of this invention, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the emulsions and elements of this invention, reference will be made to Researh Disclosure, December 1978, Item 17643, published by Industrial Opportunities Ltd., Homewell Havant, Hampshire, P09 1EF, U.K., the disclosures of which are incorporated herein by reference. This publication will be identified hereafter as "Research Disclosure".

The silver halide emulsions employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers of this invention, the elements of the invention can include additional couplers as described in Research Disclosure Section VII, paragraphs D, E, F and G and the publications cited therein. The couplers of this invention and any additional couplers can be incorporated in the elements and emulsions as described in Research Disclosure Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-N,N-diethylaniline hydrochloride, 4-amino-3-methyl-N-ethyl-N-β-(methanesulfonamido)ethylaniline sulfate hydrate, 4-amino-3-methyl-N-ethyl-N-β-hydroxyethylaniline sulfate, 4-amino-3-β-(methanesulfonamido)ethyl-N,N-diethylaniline hydrochloride and 4-amino-N-ethyl-N-(2-methoxyethyl)-m-toluidine di-p-toluene sulfonic acid.

With negative working silver halide this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following examples further illustrate this invention.

EXAMPLE 1—PREPARATION OF COUPLER 8

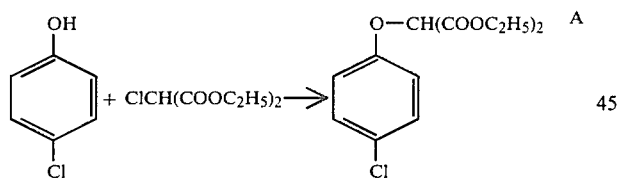

A 3-neck liter flask, fitted with a paddle stirrer and reflux condenser was charged with 12.9 g (0.1 mole) of p-chlorophenol, 19.5 (0.1 mole) diethylchloromalonate, 27.6 g (0.2 mole) potassium carbonate and 300 ml of acetone. The mixture was refluxed and stirred overnight. The solution was filtered and poured into 1400 ml of water. The resulting mixture was extracted several times with ethyl acetate. The combined extracts were dried, filtered and concentrated under reduced pressure. There was obtained 25.1 g of compound A. Thin-layer chromatography showed one main product. The material was used directly in the next step.

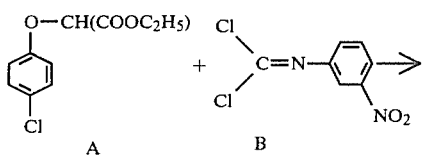

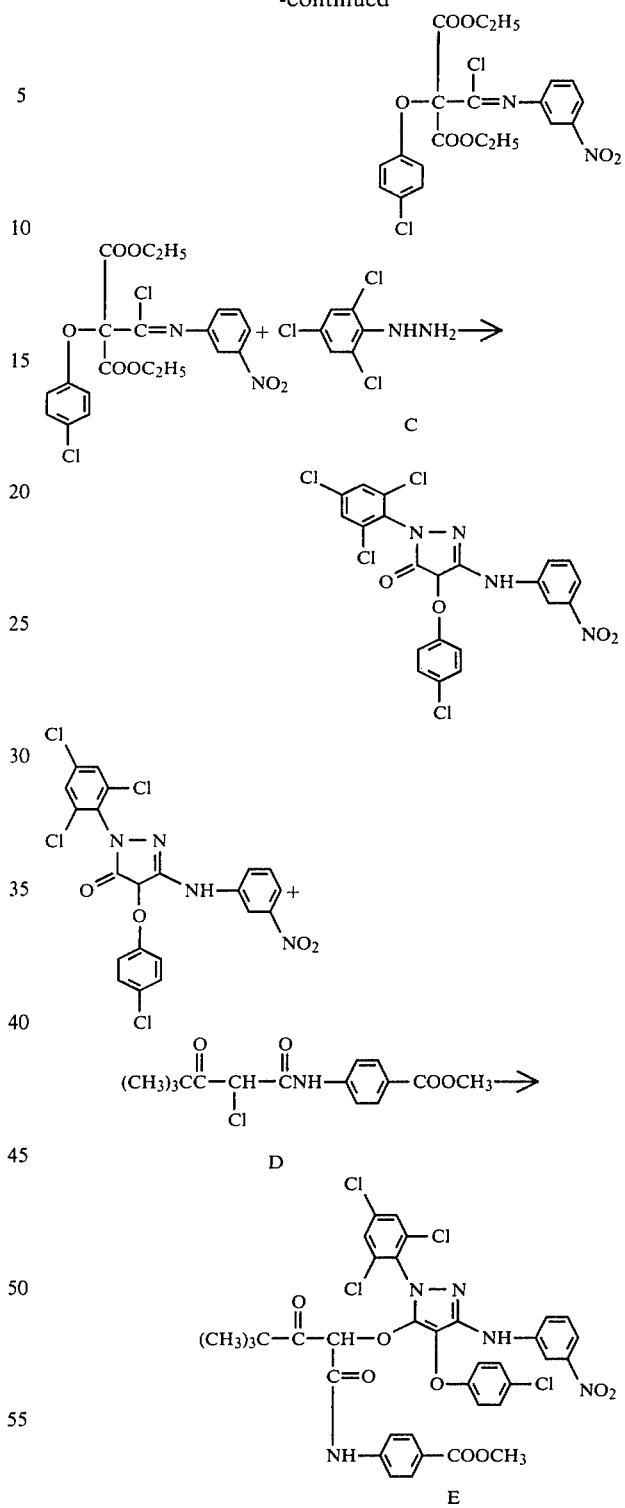

A 3-neck, 1 liter flask, fitted with stirrer and nitrogen inlet tube was charged with 11.5 g (0.1 mole) of potassium-t-butoxide in 300 ml dry tetrahydrofuran, followed by 23.6 g (0.08 mole) of compound A in 50 ml dry tetrahydrofuran, then 16.2 g (0.07 mole) of compound B in 50 ml of dry tetrahydrofuran. The mixture was stirred for one hour and then treated with 15.7 g (0.07 mole) of compound C in 250 ml of dry methanol. With vigorous stirring, 8.4 g (0.16 mole) of sodium methoxide in 50 ml of dry methanol was added dropwise over 20 minutes. The resulting mixture was stirred for one hour and the solvents were evaporated by vigorous nitrogen bubbling and gentle warming. Compound D (25.4g, 0.08 mole) in 300 ml of dry tetrahydrofuran was then added and the mixture was stirred over a weekend.

The reaction mixture was drowned in 3 liters of ice-water containing 90 ml of hydrochloric acid. The solid precipitate was collected, washed with cold water and dried in a vacuum oven at room temperature.

Three quarters of the dried solid was chromatographed on silica gel with benzene-ethyl acetate as eluent to yield 15.1 g of pure product (E). Thin-layer chromatography showed one product.

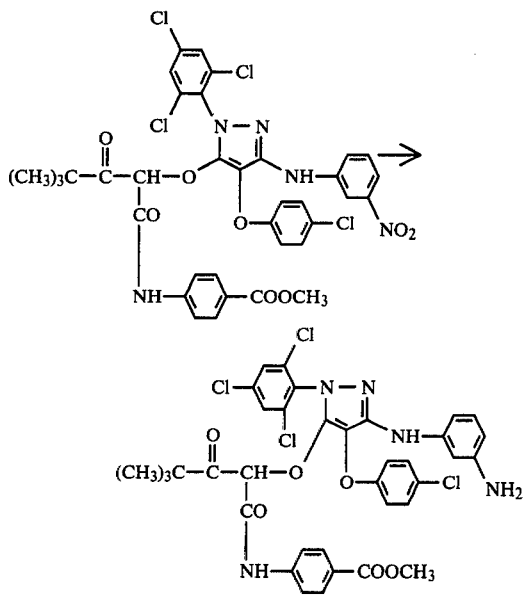

E

-continued

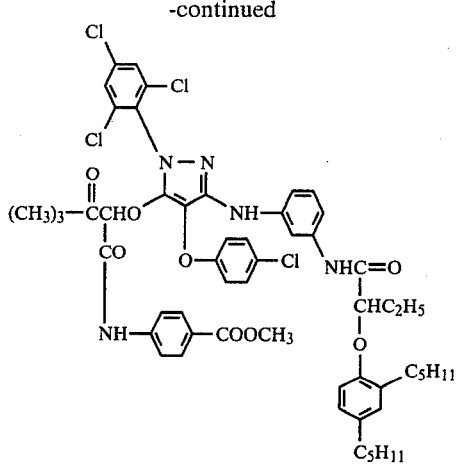

H

A pressure bottle was charged with 15.1 g (0.019 mole) of compound E, 500 ml of warm ethanol and Raney nickel catalyst, then shaken under 40 pounds of hydrogen. The theoretical amount of hydrogen was absorbed in 30 minutes.

The mixture was filtered and the filtrate was evaporated under reduced pressure to a solid residue (F). Thin-layer chromatography showed one major component.

F

A one-liter reaction flask was charged with solid residue F, 150 ml of dry tetrahydrofuran, 3.6 g of quinoline and 7 g (0.02 mole) of compound G. The mixture was stirred for two hours and added to ice-water and hydrochloric acid. The oil that settles out was separated by decantation, triturated with water and then methanol to yield a solid. The solid was collected and air dried. There was obtained 7.85 g of product H. Thin-layer chromatography showed one component.

Coupler 8

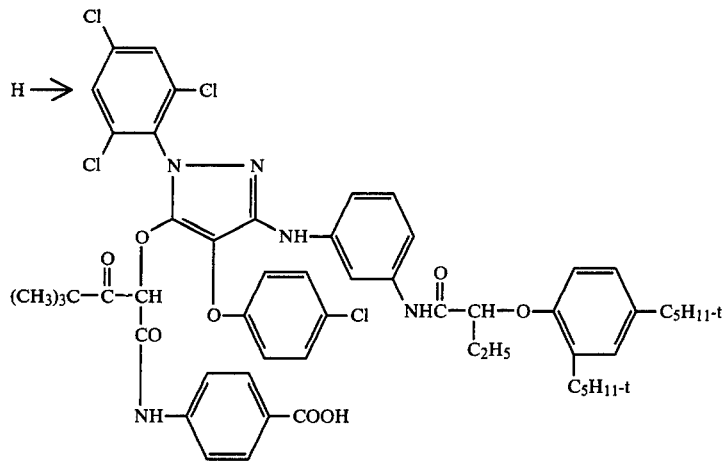

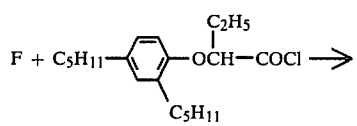

G

A reaction flask was charged with 5.7 g (0.005 mole) of compound H in 90 ml of methanol. With stirring and cooling to keep the temperature about 25° C., 12 ml of 50 percent sodium hydroxide solution was added. The mixture was warmed to 45° C. and kept there for 35 minutes. After cooling to room temperature, the mixture was allowed to stand for 4 hours and then drowned in 1 liter of ice-water containing 30 ml of hydrochloric acid. After standing overnight the solid was collected, washed with water and air dried. There was obtained 5.6 g of coupler 8.

Purification by high pressure liquid chromatography yields 2.6 g of product, m.p. 127°–129° C.

Another sample, purified by column chromatography on silica gel gives a product with melting point 128°–130° C.

Anal. Calcd. for $C_{55}H_{59}Cl_4N_5O_8$: C, 62.3; H, 5.6; Cl, 13.4; N, 6.6.

Found: C, 62.9; H, 5.9; Cl, 13.2; N, 6.5.

EXAMPLE 2

A series of photographic elements are prepared comprising a poly(ethylene terephthalate) film support having coated thereon a layer containing one of the control couplers identified in Table I. Each of the couplers was coated at 1.29 mmole/m², except for Coupler 16 which has two coupling positions and was coated at 0.65 mmole/m². Each coupler was dissolved in one half its weight of a coupler solvent, as identified in Table I. Each of the elements contained 10.08 mmoles Ag/m² of a non-spectrally sensitized silver bromoiodide emulsion and 3.01 g/m² of gelatin, except for the elements containing the 4-equivalent couplers 14 and 15 which contained 6.72 mmoles Ag/m². An overcoat layer containing 1.08 g/m² gelatin and 1.75 weight percent of bis-vinylsulfonylmethyl ether based on the total weight of gelatin was applied over the emulsion layer.

Control couplers employed were:

[Structure: 2,4,6-trichlorophenyl pyrazolone coupler with ZO substituent and anilide side chain bearing NHCCH₂O-phenyl-C₅H₁₁-t and C₅H₁₁-t groups]

| Coupler | Z |
|---------|---|
| C-I | —H |
| C-II | —CCH₃ (O=) |
| C-III | —CCH₂C₆H₅ (O=) |
| C-IV | —COC₆H₅ (O=) |

Samples of each element were incubated for three weeks at 25° C. and 80% relative humidity. Samples of incubated and nonincubated (fresh) elements were fumed with formaldehyde for one day by preconditioning air to 25° C. and 50% relative humidity and then flowing it, at 225 cc/minute, over paraformaldehyde and then over the sample. Thus, four sets of elements are obtained: (1) fresh, unfumed; (2) fresh, fumed; (3) incubated, unfumed; and (4) incubated, fumed.

Each set of elements was stepwise exposed through a graduated density test object and processed at 40° C. using the following procedure:

| Develop | 2.5 | minutes |
|---------|-----|---------|
| Stop | 2 | minutes |
| Wash | 2 | minutes |
| Bleach | 2 | minutes |
| Wash | 2 | minutes |
| Fix | 2 | minutes |
| Wash | 2 | minutes |

Formulations of processing solutions were as follows:

| Developer | | |
|-----------|---|---|
| $Na_2SO_3$(anhyd.) | 2 | g |
| 4-Amino-3-methyl-N-ethyl-N-β-hydroxyethyl-aniline sulfate | 3.55 | g |
| $K_2CO_3$ | 30 | g |
| KBr | 1.25 | g |
| KI | 0.6 | mg |
| Water to 1.0 liter, pH 10 | | |
| Stop | | |
| 3% acetic acid | | |
| pH 3 | | |
| Bleach | | |
| NaBr | 21.5 | g |
| $K_3Fe(CN)_6$ | 100 | g |
| $NaH_2PO_4 \cdot H_2O$ | 0.07 | g |
| Water to 1.0 liter, pH 7 | | |
| Fix | | |
| $Na_2S_2O_3 \cdot 0.5\ H_2O$ | 250 | g |
| $NaHSO_3$ | 1.5 | g |
| $Na_2SO_3$ | 6 | g |
| Water to 1.0 liter, pH 7. | | |

The results are recorded in Table I.

TABLE I

| Coupler | Coupler Solvent | | $D_{max}$ | | Dye Density at 0.25 g/m² Developed Ag | | % Change |
|---------|----------------|---|-----------|--------|----------|--------|----------|
| | | | Unfumed | Fumed | Unfumed | Fumed | |
| C-I | Tricresyl Phosphate | Fresh | 1.74 | 0.46 | 1.20 | 0.44 | −63.3 |
| | " | Incubated | 2.05 | 0.62 | 1.17 | 0.56 | −52.1 |
| C-II | Tricresyl Phosphate | Fresh | 0.73 | 0.60 | 0.62 | 0.52 | −16.1 |
| | " | Incubated | 1.52 | 0.82 | 1.03 | 0.74 | −28.2 |
| C-III | Tricresyl Phosphate | Fresh | 0.32 | 0.20 | 0.29 | 0.20 | −31.0 |
| | " | Incubated | 0.82 | 0.42 | 0.67 | 0.39 | −41.8 |
| C-IV | Tricresyl Phosphate | Fresh | 1.54 | 1.13 | 1.15 | 1.06 | −7.8 |
| | " | Incubated | 1.95 | 0.99 | 1.13 | 0.89 | −21.2 |
| C-I | 2,4-Di-n-amylphenol | Fresh | 1.60 | 0.82 | 1.08 | 0.70 | −35.2 |
| | " | Incubated | 1.54 | 0.85 | 1.25 | 0.82 | −34.4 |
| 1 | 2,4-Di-n-amylphenol | Fresh | 1.51 | 1.37 | 0.52 | 0.50 | −3.8 |
| | " | Incubated | 1.40 | 1.24 | 0.47 | 0.46 | −2.1 |
| 2 | 2,4-Di-n-amylphenol | Fresh | 1.64 | 1.45 | 0.49 | 0.47 | −4.1 |
| | " | Incubated | 1.49 | 1.08 | 0.48 | 0.48 | 0 |
| 14 | 2,4-Di-n-amylphenol | Fresh | 2.54 | 2.38 | 1.26 | 1.26 | 0 |
| | " | Incubated | 1.95 | 1.50 | 1.06 | 1.10 | +3.8 |
| 15 | 2,4-Di-n-amylphenol | Fresh | 1.99 | 1.82 | 1.07 | 1.07 | 0 |
| | " | Incubated | 1.71 | 1.36 | 0.89 | 0.88 | −1.1 |
| 16 | 2,4-Di-n-amylphenol | Fresh | 1.70 | 1.65 | 0.48 | 0.47 | −2.1 |

TABLE I-continued

| Coupler | Coupler Solvent | | $D_{max}$ | | Dye Density at 0.25 g/m² Developed Ag | | |
|---|---|---|---|---|---|---|---|
| | | | Unfumed | Fumed | Unfumed | Fumed | % Change |
| | " | Incubated | 1.56 | 1.35 | 0.54 | 0.54 | 0 |

Table I shows that acyl blocked pyrazolone esters (Couplers C-II, C-III and C-IV) give lower $D_{max}$ and lower dye density per unit developed silver than their unblocked analog (Coupler C-I). After incubation dye density increases, indicating unblocking during film storage. Formaldehyde fuming reduces dye density, the reduction generally being greater for incubated elements than for fresh elements. By contrast, couplers blocked according to this invention have good activity and good stability to formaldehyde fuming.

EXAMPLE 3

Additional fresh samples of the elements of Example 2 which contained control complex C-I and couplers of the invention dissolved in various coupler solvents were fumed and exposed as in Example 1 (except that fuming was for 3 days) and processed as described in *The British Journal of Photography*, 1978, pp.204-206 with the following exeptions:

| Develop | 2.5 | minutes |
|---|---|---|
| Bleach | 4 | minutes |
| Wash | 3 | minutes |
| Fix | 4 | minutes |
| Wash | 3 | minutes |
| Stabilize | 1 | minute |

Formulation of the color developer was:

| Na₂SO₃(anhyd.) | 4.0 | g |
|---|---|---|
| 4-Amino-3-methyl-N-ethyl-N-β-hydroxyethyl-aniline sulfate | 4.5 | g |
| Hydroxylamine sulfate | 2.0 | g |
| K₂CO₃ | 37.5 | g |
| NaBr | 1.4 | g |
| KI | 0.002 | g |
| 1,3-Diamino-2-propanol tetra-acetic acid | 2.5 | g |
| Water to 1.0 liter, pH 10.0. | | |

The results are recorded in Table II.

TABLE II

| Coupler | Coupler Solvent | $D_{max}$ Unfumed | Dye Density at 0.25 g/m² Developed Ag | | |
|---|---|---|---|---|---|
| | | | Unfumed | Fumed | % Change |
| C-I | 2,4-Di-n-amylphenol | 1.23 | 1.04 | 0.53 | −49.0 |
| 1 | 2,4-Di-n-amylphenol | 1.75 | 0.71 | 0.71 | 0 |
| 2 | 2,4-Di-n-amylphenol | 1.65 | 0.73 | 0.70 | −4.1 |
| 14 | 2,4-Di-n-amylphenol | 2.69 | 1.77 | 1.77 | 0 |
| 15 | 2,4-Di-n-amylphenol | 1.97 | 1.52 | 1.52 | 0 |
| 16 | 2,4-Di-n-amylphenol | 0.77 | 0.75 | 0.75 | −2.6 |
| C-I | Tricresyl Phosphate | 2.01 | 1.53 | 0.45 | −70.6 |
| 14 | Tricresyl Phosphate | 2.06 | 1.49 | 1.49 | 0 |
| C-I | Tricresyl Phosphate | 1.50 | 1.42 | 0.33 | −76.8 |
| 15 | Tricresyl Phosphate | 1.40 | 1.30 | 1.30 | 0 |

This Table shows that after fuming a high percentage of the control coupler is unavailable for dye formation while the couplers of this invention suffer no significant losses in dye yield.

EXAMPLE 4

Single layer photographic elements were prepared comprising a silver bromide emulsion and equimolar amounts of a control coupler and a coupler of this invention, as shown below. The higher silver level employed with the inventive coupler reflects its higher equivalency relative to the control coupler; i.e., 6-equivalent vs. 4-equivalent.

| Coupler | Silver (g/m²) | Coupler (g/m²) |
|---|---|---|
| 1 | 3.24 | 0.388 |
| C-I | 1.62 | 0.356 |

The photographic elements were then given a stepped exposure, developed in a color developing solution containing 4-amino-3-methyl-N-ethyl-N-β-hydroxyethylaniline sulfate for 3 minutes at 38° C., bleached, fixed, washed and dried. Density vs. Log Exposure magenta sdye curves for these coatings were well matched. RMS granularity curves show a large granularity improvement in the middle and upper scale regions for the inventive coupler compared with the control coupler.

This invention has been described in detail with particular reference to certain preferred embodiments thereof, but it will be understood that variations and modifications can be effected within the spirit and scope of the invention.

What is claimed is:

1. A photographic element comprising a support and a photosensitive silver halide emulsion having associated therewith a nondiffusible magenta dye-forming coupler having the structure:

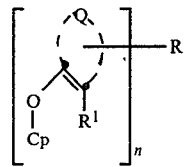

wherein:
Q represents the atoms to complete a 5-pyrazolone magenta dye-forming coupler moiety;
n is 1 or 2;
R is a ballast group when n is 1 or a divalent organic group when n is 2;
$R^1$ is hydrogen or a coupling-off group; and
Cp is a coupler moiety which upon reaction by means of oxidized color developing agent yields a colorless or alkali soluble reaction product and is attached at its coupling position to the enol oxygen of the pyrazolone coupler moiety.

2. A photographic element of claim 1 wherein the magneta dye-forming coupler has the structure:

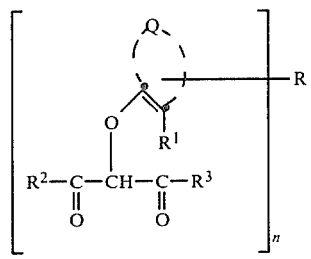

wherein:
Q represents the atoms to complete a 5-pyrazolone magenta dye-forming coupler moiety;
n is 1 or 2;
R is a ballast group when n is 1 or a divalent organic group when n is 2;
$R^1$ is hydrogen or a coupling-off group and
$R^2$ and $R^3$ represent the atoms to complete an alkali soluble yellow dye-forming coupler moiety.

3. A photographic element of claim 1 wherein the magenta dye-forming coupler has the structure:

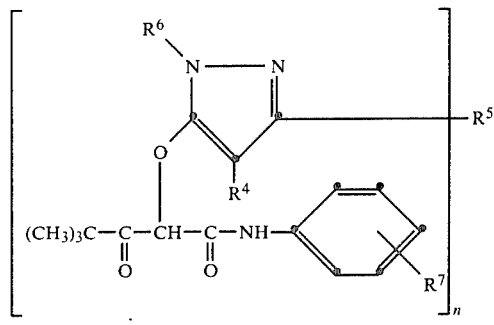

wherein:
n is 1 or 2;
$R^4$ is hydrogen or a coupling-off group;
$R^5$ is a monovalent or divalent amino or amido ballast group or an alkylene or arylene group;
$R^6$ is aryl; and
$R^7$ is one or more acid or ester solubilizing groups.

4. A photographic element of claim 3 wherein:
n is 1;
$R^4$ is hydrogen, aryloxy or arylthio;
$R^5$ is a monovalent amino or amido ballast group; and
$R^6$ is phenyl, alkoxyphenyl or halophenyl.

5. A photographic element of claim 1 wherein the magenta dye-forming coupler has one of the following structures:

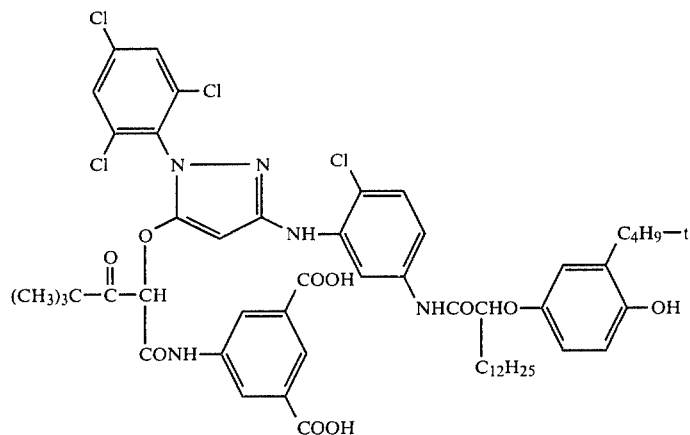

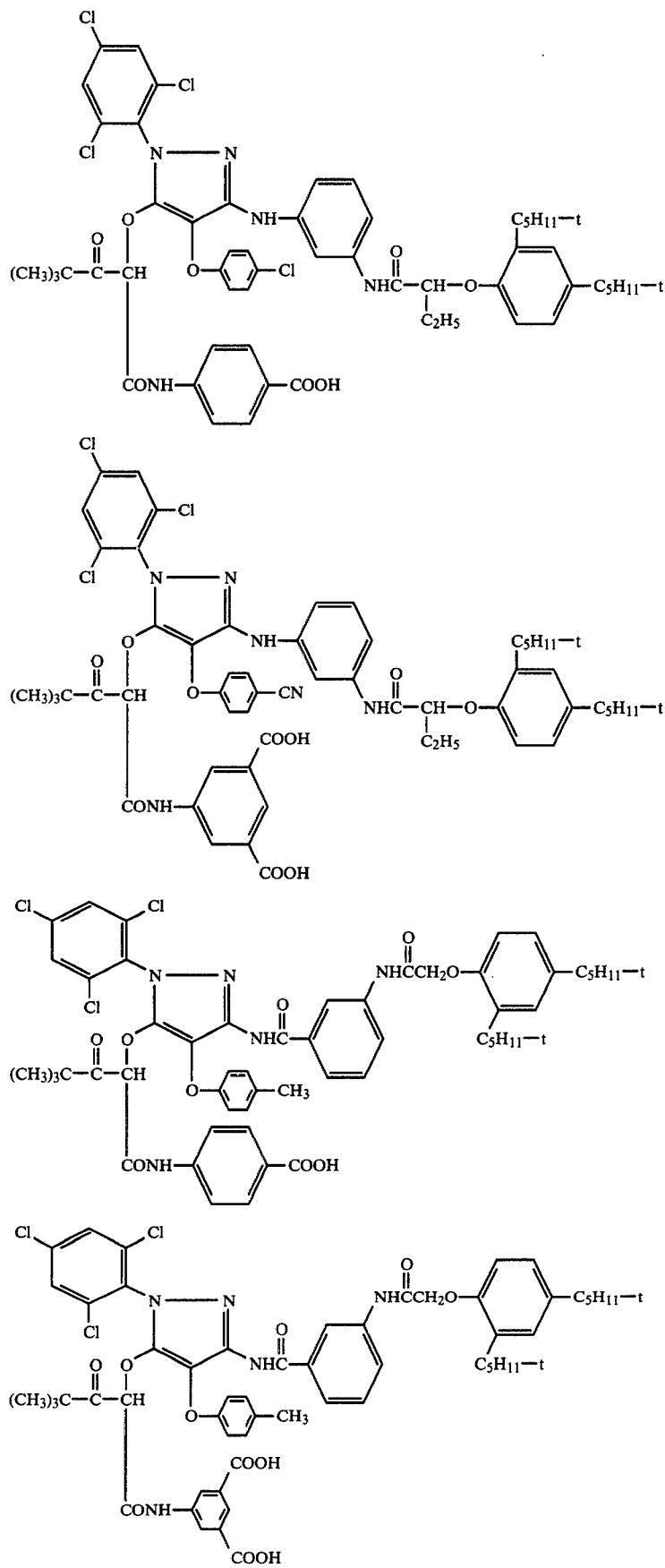

6. A photographic silver halide emulsion containing a nondiffusible magenta dye-forming coupler having the structure:

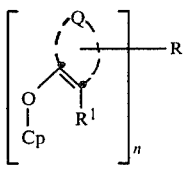

wherein:
Q represents the atoms to complete a 5-pyrazolone magenta dye-forming coupler moiety;
n is 1 or 2;
R is a ballast group when n is 1 or a divalent organic group when n is 2;
$R^1$ is hydrogen or a coupling-off group; and
Cp is a coupler moiety which upon reaction by means of oxidized color developing agent yields a colorless or alkali soluble reaction product and is attached at its coupling position to the enol oxygen of the pyrazolone coupler moiety.

7. A photographic emulsion of claim 5 wherein the magenta dye-forming coupler has the structure:

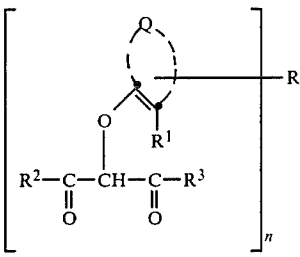

wherein:
Q represents the atoms to complete a 5-pyrazolone magenta dye-forming coupler moiety;
n is 1 or 2;
R is a ballast group when n is 1 or a divalent organic group when n is 2;
$R^1$ is hydrogen or a coupling-off group and
$R^2$ and $R^3$ represent the atoms to complete an alkali soluble yellow dye-forming coupler moiety.

8. A photographic emulsion of claim 5 wherein the magenta dye-forming coupler has the structure:

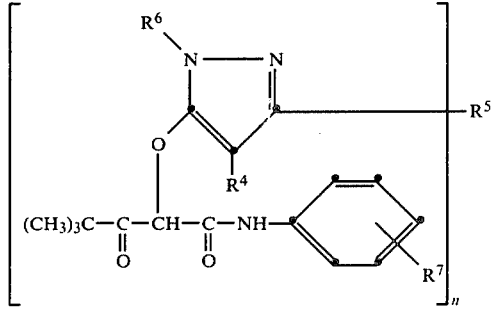

wherein:
n is 1 or 2;
$R^4$ is hydrogen or a coupling-off group;
$R^5$ is a monovalent or divalent amino or amido ballast group or an alkylene or arylene group;
$R^6$ is aryl; and
$R^7$ is one or more acid or ester solubilizing groups.

9. A photographic emulsion of claim 7 wherein
n is 1;
$R^4$ is hydrogen, aryloxy or arylthio;
$R^5$ is a monovalent amino or amido ballast group and
$R^6$ is phenyl, alkoxyphenyl or halophenyl.

10. A process of forming a magenta dye image in a photographic element comprising a support and a silver halide emulsion, comprising the step of developing the element with a silver halide color developing agent in the presence of a nondiffusible magenta dye-forming coupler having the structure:

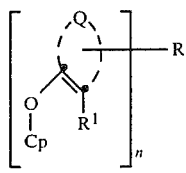

wherein:
Q represents the atoms to complete a 5-pyrazolone magenta dye-forming coupler moiety;
n is 1 or 2;
R is a ballast group when n is 1 or a divalent organic group when n is 2;
$R^1$ is hydrogen or a coupling-off group; and
Cp is a coupler moiety which upon reaction by means of oxidized color developing agent yields a colorless or alkali soluble reaction product and is attached at its coupling position to the enol oxygen of the pyrazolone coupler moiety.

11. A process of claim 10 wherein the color developing agent is a p-phenylenediamine.

12. A processed photographic element containing a magenta dye image comprised of a magenta dye obtained by coupling of oxidized silver halide color developing agent and a nondiffusible magenta dye-forming coupler having the structure:

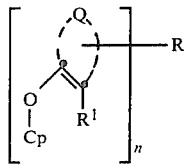

wherein:
Q represents the atoms to complete a 5-pyrazolone magenta dye-forming coupler moiety;
n is 1 or 2;
R is a ballast group when n is 1 or a divalent organic group when n is 2;
$R^1$ is hydrogen or a coupling-off group; and
Cp is a coupler moiety which upon reaction by means of oxidized color developing agent yields a colorless or alkali soluble reaction product and is attached at its coupling position to the enol oxygen of the pyrazolone coupler moiety;
there remaining in areas where magenta dye has not been formed, the blocked magenta dye forming coupler.

13. A processed photographic element of claim 12 wherein the magenta dye-forming coupler has the structure:

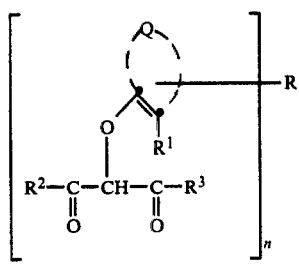

wherein:
- Q represents the atoms to complete a 5-pyrazolone magenta dye-forming coupler moiety;
- n is 1 or 2;
- R is a ballast group when n is 1 or a divalent organic group when n is 2;
- $R^1$ is hydrogen or a coupling-off group and
- $R^2$ and $R^3$ represent the atoms to complete an alkali soluble yellow dye-forming coupler moiety.

14. A processed photographic element of claim 13 wherein the magenta dye-forming coupler has the structure:

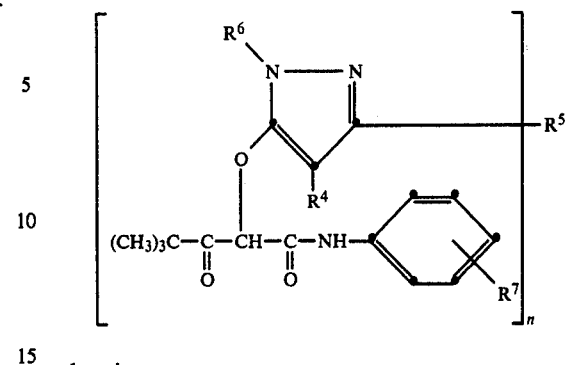

wherein:
- n is 1 or 2;
- $R^4$ is hydrogen or a coupling-off group;
- $R^5$ is a monovalent or divalent amino or amido ballast group or an alkylene or arylene group;
- $R^6$ is aryl; and
- $R^7$ is one or more acid or ester solubilizing groups.

15. A processed photographic element of claim 14 wherein:
- n is 1;
- $R^4$ is hydrogen, aryloxy or arylthio;
- $R^5$ is a monovalent amino or amido ballast group; and
- $R^6$ is phenyl, alkoxyphenyl or halophenyl.

16. A processed photographic element of claim 13 wherein the magenta dye-forming coupler has one of the following structures:

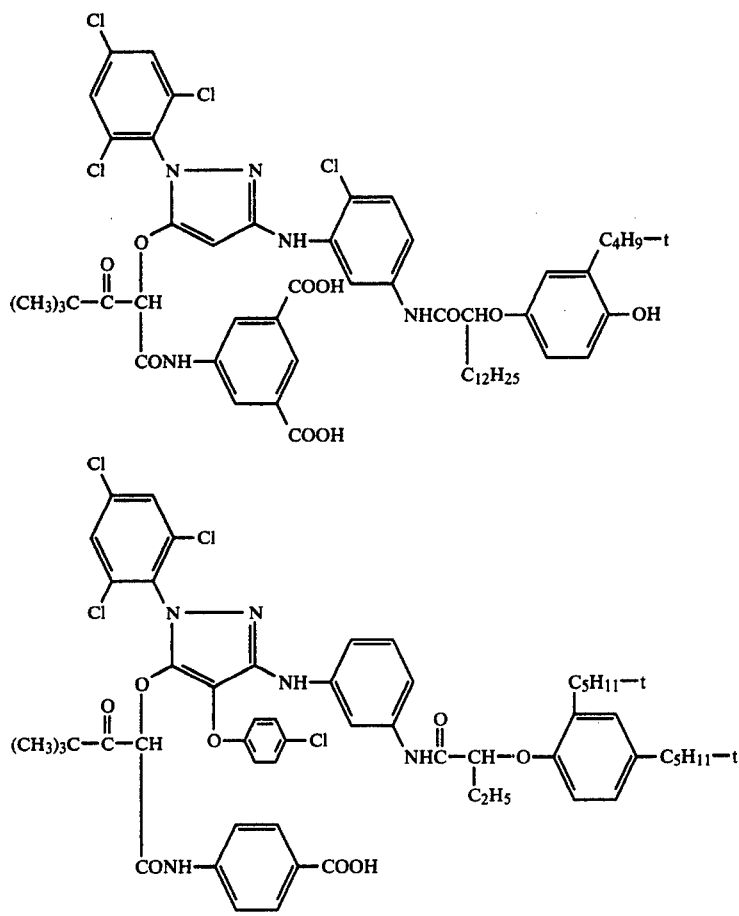

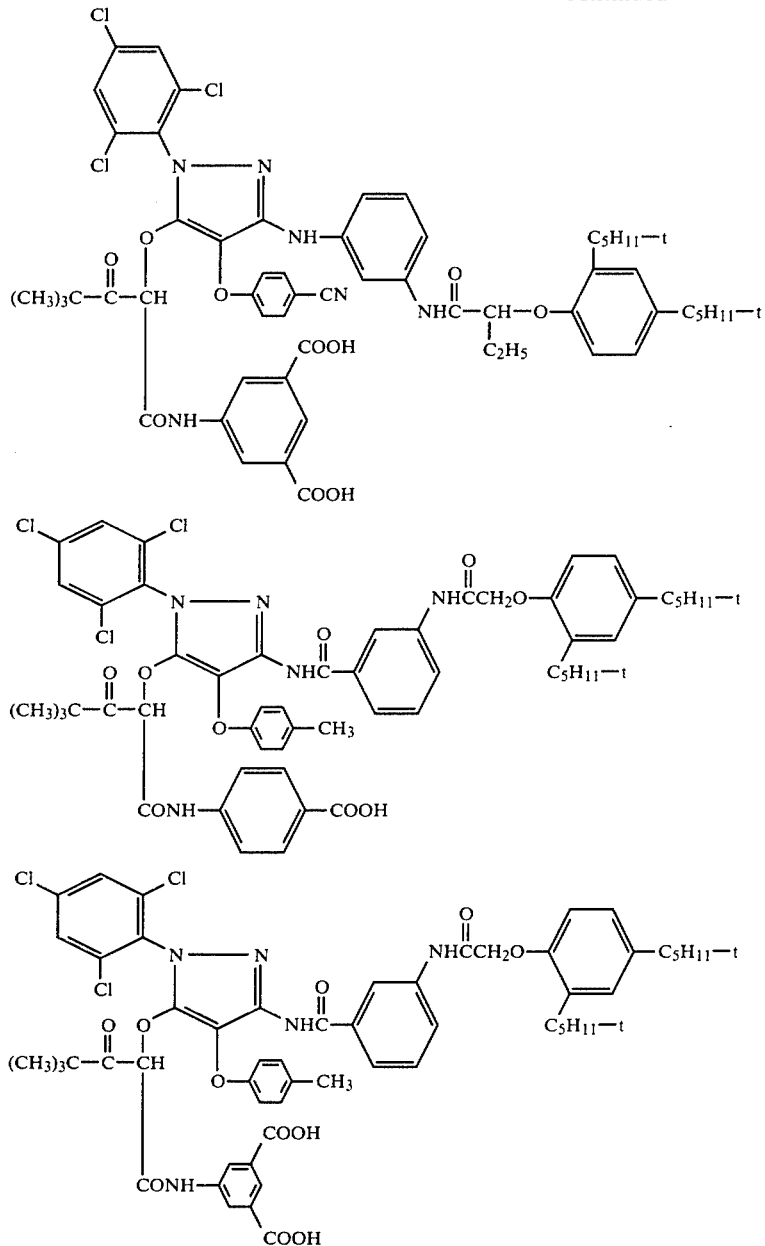
17. A processed photographic element of any one of claims 12, 13, 14, 15 or 16 wherein the color developing agent is a p-phenylenediamine.
18. A processed photographic element of claim 17 wherein the color developing agent is 4-amino-3-methyl-N-ethyl-N-β-hydroxyethylaniline sulfate.
* * * * *